United States Patent [19]
Ciabatti et al.

[11] Patent Number: 5,491,128
[45] Date of Patent: Feb. 13, 1996

[54] AGLYCONS OF A/16686 ANTIBIOTICS

[75] Inventors: Romeo Ciabatti, Brodolini; Bruno Cavalleri, Pierlombardo, both of Italy

[73] Assignee: Gruppo Lepetit S.p.A., Gerenzano, Italy

[21] Appl. No.: 425,693

[22] Filed: Apr. 19, 1995

Related U.S. Application Data

[63] Continuation of Ser. No. 315,030, Sep. 28, 1994, abandoned, which is a continuation of Ser. No. 210,119, Mar. 17, 1994, abandoned, which is a continuation of Ser. No. 73,252, Jun. 7, 1993, abandoned, which is a continuation of Ser. No. 880,613, May 8, 1992, abandoned, which is a division of Ser. No. 670,378, Mar. 14, 1991, abandoned, which is a continuation of Ser. No. 336,262, Apr. 11, 1989, abandoned.

[30]  Foreign Application Priority Data

Apr. 13, 1988 [GB] United Kingdom ............... 8808658

[51] Int. Cl.$^6$ ............... C07K 7/54; A61K 38/12; A61K 38/15
[52] U.S. Cl. ............... 514/11; 530/317; 530/323
[58] Field of Search ............... 530/317, 323; 514/11

[56] References Cited

U.S. PATENT DOCUMENTS

| | | | |
|---|---|---|---|
| 4,303,646 | 12/1981 | Cavalleri et al. | 424/118 |
| 4,427,656 | 1/1984 | Cavalleri et al. | 424/118 |
| 4,661,470 | 4/1987 | Malabarba et al. | 530/317 |
| 5,108,988 | 4/1992 | Ciabatti et al. | 514/11 |

FOREIGN PATENT DOCUMENTS 0259870   3/1988   European Pat. Off. .

OTHER PUBLICATIONS

Morita et al., J.C.S. Chem. Comm. pp. 874–875 (1978).

Cavalleri et al., The Journal of Antibiotics, vol. XXXVII, No. 4, pp. 309–317 (Apr. 1984).

Cavalleri et al., The Journal of Antibiotics, vol. XL, No. 1, pp. 49–59 (Jan. 1987).

*Primary Examiner*—Christina Y. Chan
*Attorney, Agent, or Firm*—J. Michael Dixon

[57]   ABSTRACT

The invention concerns the aglycons of factors A1, A2, A3, A'1, A'2, A'3 of antibiotic A/16686, their corresponding tetrahydroderivatives and mixtures thereof. The aglycons are produced by the selective hydrolysis of antibiotic A/16686 factor A1, A2, A3, A'1, A'2 or A'3. The compounds have antibacterial activity against widely diffused gram positive bacteria and are particularly useful for topical treatment of wound infections and acne.

6 Claims, 3 Drawing Sheets

U.V. Spectrum of factor A2 aglycon

AGLYCONS OF A/16686 ANTIBIOTICS

This is a continuation of application Ser. No. 08/315,030, filed Sep. 28, 1994, now abandoned, which is a continuation of application Ser. No. 08/210,119, filed Mar. 17, 1994, now abandoned, which is a continuation of Ser. No. 08/073,252, filed Jun. 7, 1993, now abandoned, which is a continuation of Ser. No. 07/880,613, filed May 8, 1992, now abandoned, which is a divisional of Ser. No. 07/670,378, filed Mar. 14, 1991, now abandoned, which is a continuation of 07/336, 262, filed Apr. 11, 1989, now abandoned.

This invention regards depsipeptidic compounds of following structure formula I wherein:
R represents -CO-CH=CH-CH=CH-CH$_2$-CH$_2$-CH$_3$ , -CO-CH=CH-CH=CH-CH$_2$-CH(CH$_3$)$_2$, -CO-CH=CH-CH=CH-CH$_2$-CH$_2$-CH(CH$_3$)$_2$ and the corresponding tetrahydrogenated radicals,
and the acid addition salts thereof including their mixtures in any proportion, the process for their preparation and their use as antibiotics.

The above mentioned substances are correlated with antibiotic A/16686 and are produced by selective hydrolytic treatment of the compounds identified as antibiotic A/16686 factors A1, A2, A3, A'1, A'2, and A'3, their corresponding tetrahydrogenated derivatives and the mixtures thereof.

Antibiotic A/16686 is a substance active against gram-positive bacteria described in U.S. Pat. No. 4,303,646 together with its manufacture process and the pharmaceutical compositions containing it.

It was then found that three closely related components could be isolated from antibiotic A/16686 which were named factors A1, A2 and A3. These substances as well as their preparation and uses are described in U.S. Pat. No. 4,427,656. Factor A2 is the component obtained in preponderant amount and is the most relevant for the biological activity, while factors A1 and A3 are obtained in a minor amount.

A method for selectively enhancing the production of factors A2 and/or A3 of antibiotic A/16686 by adding appropriate precursors to an A/16686 producing culture is described in European Patent Application Publication No. 259780.

European Patent Application Serial No. 88116947.8 (corresponding to U.S. patent application Ser. No. 266543 filed on Nov. 3, 1988, now abandoned) describes antibiotic A/16686 factors A'1, A'2 and A'3 and their preparation.

Antibiotic A/16686 factors A'1, A'2 and A'3 (hereinafter factors A'1, A'2 and A'3) may be produced by fermentation of Actinoplanes sp. ATCC 33076, a strain which has been deposited with the permanent culture collection ATCC as described in U.S. Pat. No. 4,303,646 and is now freely available and accepted under the Budapest Treaty as of Jan. 31, 1981, or a producing mutant thereof (i.e., natural or artificial mutant capable of producing the same substances) under submerged aerobic conditions, in an aqueous nutrient medium containing assimilable sources of carbon and nitrogen and inorganic salts. To produce workable amounts (in this case, the term "workable amounts" is intended to mean that the amount of factors A'1, A'2, and A'3 contained in the crude isolate from the fermentation broth is sufficient to permit their isolation with the usual separation and purification techniques in a quantity suitable for experimental purposes and practical utilization) of the three above mentioned compounds in the crude fermentation product, the fermentation media must contain appropriate sources of the essential elements mentioned above.

Preferred carbon sources are sugars such as dextrose, fructose, maltose, sucrose and the like, polyols such as glycerol and the like, starch and modified starches such as dextrin, with sucrose, glycerol and dextrin being the most preferred. However, it appears that when the concentration of dextrose in the nutrient culture medium is moderate or low, this has a positive effect on the formation of factors A'1, A'2, and A'3 as it can be inferred from their larger proportion in the crude isolate from the fermentation broth.

Preferred nitrogen sources are soybean meal, peptone, tryptone, malt extract, yeast extract, aminoacids and the like with soybean meal and malt extract being the most preferred.

Among the inorganic salts which are usually incorporated in the culture media are the customary soluble salts capable of yielding sodium, potassium, iron, zinc, cobalt, manganese, magnesium, calcium, ammonium, chloride, iodide, carbonate, sulfate, nitrate ions and the like.

Addition of appropriate precursors during the fermentation according to the procedure described in European Patent Application Publication No. 0259780 may be useful to, selectively increase the ratio of one of the A'1, A'2, or A'3 factors over the others. For instance, addition of from 0.2 g/l to 5 g/l of leucine (or its salts) increases the ratio of factor A'2 relative to factors A'1 and A'3 while addition of from 0.2 g/l to 5 g/l of valine (or its salts) selectively increases the relative ratio of factor A'3. Isovaleric acid has the same effect as leucine while isobutyric acid has the same effect as valine.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The producing-strain can be grown at temperatures between 20° and 40° C., preferably between 24° and 35° C., most preferably between 28° and 32° C. for a period of time (generally varying from 30 to 180 hours) during which an increase of antibiotic activity is observed.

During fermentation, the antibiotic production can be monitored by testing broth or mycelial extract samples for antibiotic activity, for instance, by bioassays or TLC or HPLC procedures.

Sensitive organisms to the antibiotics such as *Bacillus subtilis* or *Bacillus pumilus* can be used as test organisms. The bioassay is conveniently performed by the agar diffusion method on agar plates.

Maximum production of antibiotic activity generally occurs between the third and the fifth day after inoculation.

The antibiotics produced during fermentation of the strain Actinoplanes sp. ATCC 33076 are found mainly in the mycelial mass. Therefore, factors A'1, A'2 and A'3 are suitably recovered by separating the mycelium from the fermentation broth, extracting the mycelial mass with an appropriate solvent system, isolating the crude fermentation product from said extract, separating and purifying the above antibiotic substances from the isolated crude fermentation product. A preferred method of recovering the A/16686 factor A'1, A'2 and A'3 antibiotics comprises extraction of the wet mycelium after separation from the fermentation broth by filtration at a pH between 4.5 and 5.5.

Extraction of the mycelial mass is best accomplished with water miscible organic solvents such lower alkanols, acetone and their mixtures at a pH between 1.5 and 2.5.

A crude fermentation product (the "crude"), which is a mixture of A/16686 antibiotics, i.e., factor A1, A2 and A3 (U.S. Pat. No. 4,427,656) admixed with factors A'1, A'2 and A'3 together with impurities, side products, salts, filter aids and materials deriving from the fermentation broth components, is recovered from the extracting solvent(s) by routine procedures.

The isolation of factors A'1, A'2 and A'3 from the crude fermentation product, their separation and purification is conducted according to known per se techniques which include extraction with solvents, precipitation by adding non-solvents or by changing the pH of the solution, partition chromatography, reverse-phase partition chromatography, b13ion-exchange chromatography, affinity chromatography, HPLC techniques and the like.

According to a typical method of recovering the "crude" (factors A'1, A'2 and A'3), the mycelial extract in a mixture of water and water miscible organic solvents at acidic pH, which contains the above antibiotics in the form of acid addition salt, is usually extracted with an organic solvent poorly miscible with water and having a high dissolving power for lipophilic compounds (e.g., ethyl acetate, ethyl ether, n-hexane) then the aqueous layer is concentrated under vacuum. The concentrated solution is then brought to pH 7 by addition of diluted alkali or ammonia and then filtered or centrifuged to recover the solid. Filter aids can be also added to the mixture to favor the recovery of the solid product.

The wet "crude" cake obtained can be further elaborated for isolation and purification of the factors A'1, A'2 and A'3.

If a filter aid has been added before filtration it may be necessary to submit the "crude" cake to a further extraction with a mixture of water and a water miscible organic solvent at acidic pH like to the one applied for the extraction of the mycelial cake.

Re-precipitation of the "crude" from this extract is carried out by decreasing the solubility of the acid addition salts of factors A'1, A'2 and A'3 in the extract by adding thereto a water miscible organic solvent wherein said acid addition salts are poorly soluble. Acetone and isopropanol are suitable organic solvents for said purpose.

The wet crude isolate is then further purified for eliminating therefrom most of the non-A/16686 antibiotic products. Thus, sludging the crude wet cake with a diluted (5 to 10% w/v)) solution of a strong mineral acid followed by centrifugation is useful for eliminating some of the impurities. The wet cake thus obtained may be further purified by re-dissolving in a mixture of water and water soluble organic solvent of the same type as those employed for the extraction of the mycelial cake at a pH between 1.5 and 2.5. During this operation, decolorizing agents can be added to the aqueous solution. Precipitation of the purified fermentation product (containing factors A'1, A'2 and A'3) from the acidic solution may be carried out according to the procedure described above. Such purified preparation of the fermentation product is essentially consisting of a mixture of factors A'1, A'2 and A'3 together with one or more other similar products, i.e., the factors A1, A2 and A3 of antibiotic A/16686. Isolation of factors A'1, A'2, and A'3 from the above described mixture is carried out by the usual separation techniques as mentioned above. Preparative HPLC is particularly useful for both separation and purification purposes when the fermentation products contain considerable amount of antibiotic A/16686 factors A1, A2 and A3. The preparative HPLC operations are usually conducted under conditions which are common to the separation and purification of the A/16686 antibiotic. Examples of said separation and purification operations can be found, for instance, in U.S. Pat. No. 4,427,656 where a C-18 alkyl silanized silicagel column and an eluent mixture of aqueous ammonium formate and acetonitrile are employed.

During the preparative HPLC the eluted liquids from each injection are checked by analytical HPLC and those fractions enriched in A/16686 factor A'1, A'2 and A'3, respectively, are separated.

The fractions enriched in each of the above compounds are combined and concentrated to dryness under vacuum. The respective solid residues are re-submitted to preparative HPLC under the same conditions as before. The solid products resulting from concentration of the eluted solutions are dissolved in diluted mineral acids and freeze-dried to yield the respective pure products under the form of mineral acid addition salts.

An alternative method for producing factors A'1, A'2 and A'3 consists in contacting a substrate containing antibiotic A/16686 factor A1, A2 and A3 or a mixture thereof with the mycelium of Actinoplanes sp. ATCC 33076 or a natural or artificial mutant thereof capable of producing A/16686 antibiotics, thus promoting the biotransformation into factors A'1, A'2 and A'3. According to this procedure, the single factors A1, A2 and A3 or a mixture thereof, such as, for instance, the complex resulting from a fermentation operation, are allowed to contact the mycelium for a period of time ranging from 50 to 200 hours at a temperature between 28° and 35° C., preferably between 29° and 33° C. This operation may be sequential to the fermentation of Actinoplanes sp. ATCC 33076 (or a producing mutant thereof) for producing the A/16686 antibiotics and therefore may consist in a prolonged contact of the fermentation product with the mycelium. When the fermentation operations have been carried out according to the conditions described above, the fermentation product already contains some amounts of factor A'1, A'2 and A'3 and, therefore, a prolonged contact with the mycelium actually results in an enrichment of the ratios of said compounds in the fermentation batch.

According to a practical embodiment of this method, after the fermentation cycle is complete, i.e., when analytical tests show that the antibiotic activity in the fermentation broth is no longer increasing, inlet of oxygen (or air) into the fermentors is stopped and the fermentation broth is kept with stirring at a temperature between 29° and 33° C. for an additional period of time varying from 50 to 200 hours before harvesting under analytical HPLC control.

A preferred mode to carry out the biotransformation of the factor A1, A2 and A3 into the corresponding factor A'1, A'2 and A'3 consists in contacting the first three substances mentioned above (or a mixture thereof, including the A/16686 complex as resulting from the recovery operations from the fermentation batch, as described, for instance, in U.S. Pat. No. 4,303,646) with the isolated mycelium of Actinoplanes sp. ATCC 33076 or a producing natural or artificial mutant thereof. Mycelium grown in a suitable culture medium is isolated from the fermentation broth (e.g. by centrifugation) and then added to a solution of factor A1, A2 or A3 or a mixture thereof in water or in a mixture of water and one or more organic solvents mixable with water (e.g. lower alkanols or acetone) with stirring. The temperature of the reaction mixture is maintained within the range indicated above while the pH may be kept steady around 7 by buffering the solution with a suitable buffer (e.g. a phosphate buffer). The biological transformation is usually followed by analytical HPLC. Experimental tests show that an A/16686 antibiotic crude mixture originally containing respectively about 14 percent of factor A1, about 64 percent of factor A2 and about 12 percent of factor A3 after about 140 hours of contact with the isolated mycelium of Actinoplanes sp. ATCC 33076 under the above conditions is transformed into a mixture containing respectively about 10% factor A'1, about 38% factor A'2 and about 5% factor A'3 with a concomitant decrease of the content of factor A1, A2 and A3 to 10%, 28% and 9% (HPLC areas), respectively. Analogously, a substrate consisting of an almost pure sample of factor A2 (HPLC titre: 89%) after 180 hours is converted into a mixture containing about 60% factor A'2 with the content of factor A2 decreasing to about 33% (HPLC areas).

The products resulting from the above described biotransformation are recovered from the reaction mixture (or from the fermentation broth, in case the biological transformation is directly operated by prolonging the contact with the mycelium in the fermentation batch) by acidifying the mycelial suspension to a pH between 1.5 and 2.5 and then adding thereto a water soluble organic solvent such as a lower alkanol or acetone, if this is not already present in a sufficient amount, to help extraction of the reaction products from the mycelial mass. After separation of the mycelium by filtration or centrifugation, the solution is elaborated in the same way as described above for isolating and purifying the compounds of this invention.

When the biological transformation is directly operated on the fermentation broth as mentioned above, the recovery of the reaction products can be carried out exactly as described before, for the recovery of the fermentation products.

European Patent Application Serial No. 88119001.1 (corresponding to U.S. patent application No. 280035 filed on Dec. 5, 1988) describes the tetrahydrogenated derivatives of antibiotic A/16686 factors A1, A2, A3, A'1, A'2 and A'3 and their method of manufacture. The compounds of this invention are also identified respectively as A/16686 factor A1 aglycon, A/16686 factor A2 aglycon, A/16686 factor A3 aglycon, A/16686 tetrahydrogenated factor A1 aglycon (formula I, $R=-CO(CH_2)_6-CH_3$), A/16686 tetrahydrogenated factor A2 aglycon (formula I, $R=-CO(CH_2)_5CH(CH_3)_2$), A/16686 tetrahydrogenated factor A3 aglycon (formula I, $R=-CO(CH_2)_6CH(CH_3)_2$).

The compounds of this invention may be produced by selective hydrolysis of a starting material selected from antibiotic A/16686 factors A1, A2, A3, A'1, A'2, A'3, a mixture of two or more of them, their respective tetrahydro derivatives and a mixture of two or more of them. Accordingly, the selective hydrolysis may be carried out either on the single factors or on any mixture of two or more of them such as, for instance, the A/16686 antibiotic complex produced by fermentation of Actinoplanes sp. ATCC 33076 (a strain which has been deposited with the permanent culture collection ATCC and is now freely available and accepted under Budapest Treaty as of Jan. 31, 1981) as described in U.S. Pat. No. 4,303,646. Further examples of mixtures of the A/16686 factors are those resulting from the method of European Patent Application Publication No. 259780 whereby the ratio of the factor A2 and/or A3 is selectively increased during the fermentation process, and the mixtures containing the factors of both A and A' groups which are obtainable by fermentation of the above mentioned Actinoplanes sp. ATCC 33076 under appropriate conditions or by contacting the group A factors or a mixture thereof with the mycelium of the same strain for an appropriate period of time under proper conditions, according to the methods described in the above mentioned European Patent Application Serial No. 88116947.8 (corresponding to U.S. patent application Ser. No. 266543).

Mixtures of tetrahydrogenated factors A1, A2, A3, A'1, A'2, A'3 are for instance obtainable by hydrogenation of antibiotic A/16686 complex as described in European Patent Application Serial No. 88119001.1 (corresponding to U.S. patent application Ser. No. 280035).

In all cases mentioned above the starting materials may be either in the form of a free base or in the form of an acid addition salt such as those disclosed in U.S. Pat. Nos. 4,303,646, 4,427,656 and in the co-pending European Patent Application Serial No.88116947.8 (corresponding to U.S. patent application Ser. No. 266543).

When the starting material consists in a mixture of two or more A/16686 factors the product mixture resulting from the selective hydrolysis may be separated into the pure components corresponding to the compounds of formula I of this invention.

The expression "selective hydrolysis" as used in this description and in the claims means an hydrolysis process carried out under controlled conditions which allows splitting the semi-acetalic bond between the sugar moiety and the rest of the A/16686 molecule without affecting the other portions of the basic structure of the A/16686 antibiotics which includes peptidic, amidic and lactonic bonds.

Accordingly, a further object of this invention is a selective hydrolysis process for the manufacture of the compounds of formula I above characterized by the fact that a starting material selected from antibiotic A/16686 factors A1, A2, A3, A'1, A'2, A'3, a mixture of two or more of them, their respective tetrahydro derivatives and a mixture of two or more of them is contacted with either:

a) trimethylsilyl iodide or trimethylsilyl chloride in the presence of sodium iodide followed by hydrolysis under mild conditions of the obtained trimethylsilyl derivative or b) a strong acid in the presence of a lower alkanol or a mixture of lower alkanols under anhydrous conditions.

The selective hydrolysis procedure of paragraph a) above involves the transformation of the glycosidic acetals of the A/16686 antibiotics into the corresponding trimethylsilyl ethers according to the method described by T. Morita et al. in J.C.S., Chem. Comm. 1978, page 874 and in the references cited in the same paper.

The formation of the trimethylsilyl ethers is generically carried out in the presence of an aprotic organic solvent by contacting the starting A/16686 material with a molar excess of trimethylsilyl iodide or trimethylsilyl chloride, e.g. one to three milliliters of trimethylsilyl halogenide for each gram of starting material. When trimethylsilyl chloride is used, sodium iodide is added to the reaction mixture in a proportion ranging from 0.01 to 1 mole of sodium iodide for each mole of trimethylsilyl chloride. The aprotic organic solvent is generally selected from chlorinated lower hydrocarbons (e.g. dichloromethane, carbon tetrachloride), dimethylformamide, dimethylsulfoxide and acetonitrile and their mixtures. The temperature of the reaction is usually ranging between 10° C. and 100° C., preferably between 20° C. and 80° C.

As it may be appreciated by those skilled in the art, the reaction time may vary depending on the type and purity of the starting material and the specific reaction conditions of the process. In general, the reaction is completed in 0.5 to 5 hours. In any case, the reaction course may be monitored by TLC or HPLC techniques as known in the art. For instance, samples may be drawn at intervals and assayed in order to determine when the reaction is complete. The reaction may then be stopped in order to prevent the negative consequence of a prolonged contact of the final product(s) with the reaction mass.

The trimethylsilyl ether bonds are then easily hydrolyzed under mild conditions. The expression "mild conditions" in this case means that the reaction conditions must be appropriate for splitting the trimethylsilyl ether bond(s) without affecting the other positions of the antibiotic molecule. According to a general procedure, the reaction solution containing the trimethylsilyl derivative(s) is contacted with water or a lower alkanol or a mixture thereof at a temperature which varies from 0° C. to the room temperature by keeping the pH value between 3 and 5 and for a period of time which may vary depending on the value of the pH and the temperature and usually ranges from 0.1 to 24 hours.

Accordingly, when the silylation reaction is completed, the reaction mixture is then poured into an excess of water or a lower alkanol or a mixture thereof in the presence of an approximate amount of a mild base to maintain the pH value between 3 and 5. The reaction products of formula I are then recovered from this mixture and purified according to known methods such as evaporation, extraction with solvents, precipitation by addition of non-solvents, column chromatography and the like. Sometimes, it may be convenient to concentrate the organic solution to a small volume to precipitate the crude hydrolysis product.

The isolation of the antibiotic substances of this invention from the crude hydrolysis product, their separation and purification is conducted according to known per se techniques which include extraction with solvents, precipitation from the obtained solution by addition of non-solvents or by changing the pH of the solution, partition chromatography, reverse-phase partition chromatography, ion-exchange chromatography, affinity chromatography, HPLC techniques and the like.

When the selective hydrolysis is carried out according to the procedure of paragraph b) above, the strong acid is usually a strong mineral acid e.g. hydrochloric or hydrobromic acid or a strong aryl or alkyl sulfonic acid such as p.toluenesulfonic acid, methanesulfonic acid, ethanesulfonic acid, their halogenated derivatives such as trifluoromethanesulfonic acid, trichloromethanesulfonic acid and the like.

The strong acid may also be a dried strong cation exchange resin in the acid form. Both gel and macroporous dried resins of this type are commercially available, e.g. DOWEX® DR-2020, DR-2030, DR-2090 or DOWEX® M15-DR, M18-DR, M31-DR and M32-DR. If needed, the commercially available dried resins may be further anhydrified by repeatedly washing with anhydrous methanol, by azeotropic distillation methods or by heating at 100°–115° C. under reduced pressure. The reaction is usually carried out in the presence of a solvent that may be selected from the organic polar solvent such as dimethylformamide or dimethylsulfoxide or, even, an excess of the same lower alkanol (i.e. a $C_1$–$C_6$ alkanol) or mixture thereof. The acid is usually dissolved in a large excess of the solvent in a concentration from 1 to 5 per cent (w/v) preferably from 2 to 3.5 per cent (w/v).

According to a typical embodiment of the method under paragraph b) above, the A/16686 starting material is added to a solution (or a suspension) of the acid in in the selected solvent in the presence of an excess of lower alkanol, preferably butanol, and the mixture is maintained at a temperature between 15° and 80° C. until the splitting of the glycosidic acetal bond is completed. Also in this case, the reaction time varies depending on the type and purity of the starting materials and the specific reaction conditions. The reaction course may be monitored by TLC or HPLC techniques as indicated for the procedure according to the paragraph a) above. In general, the reaction time ranges from 0.1 to 10 hours. Also in this case, the reaction products are recovered from the reaction mixture and purified according to known methods such as those mentioned above for the procedure according to paragraph a).

When the selective hydrolysis is carried out on a substrate consisting of a mixture of two or more of the factors A1, A2, A3, A'1, A'2 and A'3 or their tetrahydro derivatives and the obtainment of the single aglycon derivatives is desired, the separation and purification of the hydrolysis product is carried out, preferably, by using column chromatography or preparative HPLC methods. The preparative HPLC operations are usually conducted under conditions which are common to the separation and purification of the A/16686 antibiotic factors. Examples of said separation and purification operations can be found, for instance, in U.S. Pat. No. 4,427,656 where a C-18 alkyl silanized silicagel column and an eluent mixture of aqueous ammonium formate and acetonitrile is employed.

During the preparative HPLC, the eluted liquids from each injection are checked by analytical HPLC and those fractions enriched in each A/16686 factor aglycon are separated.

The fractions enriched in each of the above compounds are combined and concentrated to dryness under vacuum. The solid product(s) resulting from concentration of the eluted solution(s) is/are set free from the residual salts, then dissolved in aqueous mineral acids and the resulting solutions are freeze-dried to yield the respective pure product(s) under the form of mineral acid addition salt(s), e.g., the dihydrochloride(s). The above operation can be repeated one or more times when the purity of the resulting products is not satisfactory. The column chromatography operations may be performed, for example, on silanized silicagel by using water:acetonitrile mixtures as the solvent and diluted hydrochloric acid: acetonitrile mixtures as the eluent. If needed, the products separated by column chromatography methods are further purified by preparative HPLC. Also in this case, it is usually preferred to isolate the final aglycon product under the form of a mineral acid addition salt by following the same procedure described above. If needed, the solid residues resulting from column chromatography or HPLC can be desalted by chromatography through a macroporous resin (e.g. XAD-2) and elution with an acidic solution.

Antibiotic A/16686 factors A1, A2 and A3 aglycons and their tetrahydro derivatives are submitted to acid/base titration, aminoacid analysis (for quantity and sequence), IR, UV, NMR spectrometry and Fast Atom Bombardment Mass Spectrometry (FAB-MS). The data resulting from these analytical tests confirm the assigned structures.

As shown in formula I the antibiotic substances of this invention possess two basic functions which can form acid addition salts according to conventional procedures.

Representative and suitable acid addition salts of the compounds of formula I include those salts formed by standard reactions with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic acid and the like.

The transformation of the free amino or non-salt compounds of the invention into the corresponding addition salts, and the reverse, i.e., the transformation of an acid addition salt of a compound of the invention into the non-salt form, are within the ordinary technical skill and are encompassed by the present invention.

For instance, a compound of the invention can be transformed into the corresponding acid addition salt by dissolving the non-salt form in an aqueous solvent and then adding a slight excess of the selected acid. The resulting solution or suspension is then lyophilized to recover the desired salt.

In case the final salt is insoluble in a solvent where the non-salt form is soluble, the salt is recovered by filtration from the organic solution of the non-salt form after addition of the stoichiometric amount or a slight excess of the selected acid.

When desired, the non-salt form can be obtained from a corresponding acid salt dissolved in an aqueous solvent by neutralization to set free the non-salt form.

When, following the neutralization, desalting is necessary, a common desalting procedure may be employed.

For example, column chromatography on silanized silica gel, non-functionalized polystyrene, acrylic and controlled pore polydextrane resins (such as SEPHADEX LH 20) or activated carbon may be conveniently used. After eluting the undesired salts with an aqueous solution, the desired product is eluted by means of a linear gradient or a step-gradient of a mixture of water and a polar or apolar organic solvent, such as water/acetonitrile from 50:50 to about 100 per cent acetonitrile.

As it is known in the art, the salt formation either with pharmaceutically acceptable acids or non-pharmaceutically acceptable acids may be used as a convenient purification technique. After formation and isolation, the salt form of an antibiotic of formula I above can be transformed into the corresponding non-salt or into a pharmaceutically acceptable salt.

The aglycons of A/16686 antibiotics are particularly active against gram-positive microorganisms. The microbiological activity spectrum of antibiotic A/16686 aglycons factors A1, A2 and A3 are reported in the following Table I:

TABLE I

| | In vitro activity of A/16686 antibiotic aglycons (dihydrochlorides) | | | |
|---|---|---|---|---|
| | MIC (mcg/ml) | | | |
| Strain | Factor A1 aglycon | Factor A2 aglycon | Factor A3 aglycon | A/16686 factor A2 |
| *Staphylococcus aureus* Tour | 1 | 1 | 1 | 1 |
| *Staphylococcus aureus* Tour[a] | 2 | 2 | 2 | 2 |
| *Staphylococcus aureus* Tour[b] | 1 | 2 | 1 | 1 |
| *Staphylococcus epidermidis* ATCC 12228 | 0.5 | 0.032 | 0.5 | 1 |
| *Staphylococcus haemolyticus* L 602[c] | 0.25 | 0.25 | 0.5 | 1 |
| *Streptococcus pyogenes* C203 SKF 13400 | 0.008 | 0.032 | 0.008 | 0.063 |
| *Streptococcus pneumoniae* UC41 | 0.016 | 0.032 | 0.016 | 0.063 |
| *Streptococcus faecalis* ATCC 7080 | 1 | 0.5 | 1 | 1 |
| *Streptococcus mitis* L 796[c] | 0.125 | 0.063 | 0.125 | 0.125 |
| *Propionibacterium acnes* ATCC 6922 | 0.063 | 0.125 | 0.25 | 0.25 |
| *Propionibacterium acnes* L 1557[c] | 0.063 | 0.125 | 0.5 | 0.25 |
| *Propionibacterium acnes* L 1559[c] | 0.125 | 0.125 | 0.5 | 0.25 |
| *Propionibacterium acnes* L 1563[c] | 0.125 | 0.125 | 0.25 | 0.25 |
| *Propionibacterium acnes* L 1565[c] | 0.125 | 0.125 | 0.5 | 0.25 |

[a] Inoculum $10^6$ cfu/ml
[b] 30% bovine serum added
[c] Clinical isolates

Minimal Inhibitory Concentration (MIC) is determined by either the broth (tube) or the agar serial two-fold dilution method. Culture media and growth conditions:

ISO-SENSITEST BROTH (Oxoid), for *staphylcocci* and *Streptococcus faecalis;* TODD-HEWITT BROTH (Difco), for other streptococcal species; WILKINS-CHALGREN AGAR for *P. acnes* (T. D. Wilkins, S. Chalgren: Antimicrob. Agents Chemother. 10,926 (1976); unless indicated otherwise, the final inoculum is of about $10^4$ colony-forming units/ml or spot. MIC is read as the lowest concentration which shows no visible growth after 18–24 hours incubation at 37° C.; for anaerobs the incubation is at 37° C. for 48 hours in anaerobic atmosphere ($N_2:CO_2:H_2$, 80:10:10).

The activity of the tetrahydro derivatives of the aglycons in the same experiments are of the same level as those of the aglycons reported above. Since A/16686 aglycon factor A2 shows good activity against *S. epidermidis* it has been tested against a series of *S. epidermidis* clinical isolate pathogens of relevant clinical interest (Table II):

TABLE II

In vitro activity of A/16686 factor A2 aglycon
(dihydrochloride) against selected
*Staphylococcus epidermidis* strains (clinical isolates)

| Organism | MIC (mcg/ml) | |
|---|---|---|
| | Factor A2 aglycon | Antibiotic A/16686 factor A2 |
| *Staphylococcus epidermidis* L 354 | 0.5 | 0.5 |
| *Staphylococcus epidermidis* L 357 | 1 | 1 |
| *Staphylococcus epidermidis* L 393[a] | 0.125 | 1 |
| *Staphylococcus epidermidis* L 420[a] | 0.125 | 0.5 |
| *Staphylcoccus epidermidis* L 576 | 0.125 | 0.5 |
| *Staphylococcus epidermidis* L 580[a] | 0.25 | 0.5 |
| *Staphylococcus epidermidis* L 586 | 0.032 | 0.25 |
| *Staphylococcus epidermidis* L 600[a] | 0.125 | 1 |
| *Staphylococcus epidermidis* L 619[a] | 0.125 | 0.5 |
| *Staphylococcus epidermidis* L 838[a] | 0.063 | 0.5 |
| *Staphylococcus epidermidis* L 848[a] | 0.5 | 1 |
| *Staphylococcus epidermidis* L 874[a] | 0.032 | 1 |
| *Staphylococcus epidermidis* L 1065 | 0.032 | 0.5 |
| *Staphylococcus epidermidis* L 1067 | 0.032 | 0.5 |
| *Staphylococcus epidermidis* L 1378 | 0.25 | 1 |
| *Staphylococcus epidermidis* L 1471 | 0.5 | 1 |
| *Staphylococcus epidermidis* L 1480 | 0.5 | 1 |
| *Staphylococcus epidermidis* L 1575[a] | 0.5 | 1 |
| *Staphylococcus epidermidis* L 1578[a] | 0.125 | 0.5 |
| *Staphylococcus epidermidis* L 1579 | 0.032 | 0.5 |

[a] methicillin-resistant

Antibiotic A/16686 aglycons are active also in mice infected with *Streptococcus pyogenes*. In a representative experiment, groups of five mice (Charles River) are infected intraperitoneally with *S. pyogenes* C 203 SKF 13400. Inocula were adjusted so that untreated animals died of septicemia within 48 hours. Immediately after infection, animals are treated subcutaneously once with A/16686 factor A2 aglycon. On the 10th day the value for the $ED_{50}$ in mg/kg is calculated by the method of Spearman and Karber (Finney, D. J., Statistical Methods in Biological Assay p. 524; C. Griffin and Co., London, 1952), on the basis of the percentage of surviving animals at each dose.

The ED50 shown by A/16686 factor A2 aglycon is of 0.11 mg/kg (in comparison with 0.14 for antibiotic A/16686 factor A2).

The antibiotic compounds of this invention are useful for preparing medicaments against infections primarily due to gram-positive widely diffused bacteria. In particular, the compounds of this invention are useful for topical treatment of skin and wound infections and acne.

For use as medicaments the compounds of this invention can be administered by different routes either in the form of free compounds or in the form of their addition salts with pharmaceutically acceptable acids, this latter form being preferred. For the medical uses the compounds of this invention are incorporated into pharmaceutical dosage forms suitable for oral, topical or parenteral administration such as tablets, capsules, lozenges, gelules, granules, powders, ointments, gels, liquid solutions, creams, solutions for injections, suspensions and the like. For instances, the formulations of said dosage forms can be carried out according to the general teaching of Remington's Pharmaceutical Sciences 17th Edition, 1985 Merck Publishing Company, Easton Pa. The topical route is usually the most suitable way to administer the compounds of this invention.

The dosage unit may contain from 0.01 to 99 percent preferably from 0.5 to 80 percent of active ingredient. The daily dosage may depend on several factors such as body weight, the infecting microorganism, the severity of the infection, the age of the patient, the period and the way of administration. In general, the compounds of this invention are effective at a daily dosage ranging from about 2 mg to about 100 mg per kilogram of body weight, optionally divided into one or more administrations per day. In particular, for topical administration, ointments, creams, solutions, gels and lotions may have either a hydrophilic or hydrophobic base and preferably contain from 0.1 to 15 percent by weight of active ingredient. The topical dosage forms may contain also sorption promoters (see for instance: W. A. Ritschel and O. L. Sprockel, Drugs of Today, Vol. 24, pages 613–628, 1988) and preservatives. Obviously, the above dosages are only indicative and the most appropriate dosage can be adjusted in the specific cases and applications by relying on biological testings useful for determining the amount of active compound required to produced the desired effect.

The following examples have the purpose to illustrate the invention but should not be construed as a limitation of its scope.

EXAMPLES

Example 1

A/16686 factor A2 aglycon

To a mixture of 10 ml of dimethylformamide and 10 ml of acetonitrile, sodium iodide (50 mg) and A/16686 factor A2 (obtained according to U.S. Pat. No. 4,427,656) (1 g) is added, followed by 2 ml of trimethylsilyl chloride. The suspension becomes clear. After heating at 75° C. for 2 hours, 90 mg of sodium iodide is added, and the reaction mixture is heated for further 1 hour at 75° C.

After cooling water is added, the pH is brought at 4 with $NaHCO_3$ and the reaction mixture is extracted with butanol three times. The butanolic layer is separated and evaporated under vacuum while toluene is repeatedly added to the solution. The solid residue (1.25 g) is submitted to preparative HPLC by using the following apparatus for each portion of 250 mg dissolved in 5 ml of a mixture of water and acetonitrile 1:1 (v/v). Instrument: the apparatus is set up by assembling a Waters mod. 590 pump, a WATERS LAMBDA-MAX (model 481LC) detector set at 254 nm, and a Rheodyne injector equipped with a 5 ml loop.

Column: LICHROSORB RP-18, 10 micron, 250 mm×50 mm (Merck)

Mobile phase: 0.05 M $HCOONH_4:CH_3CN$ (60:40)

Flow rate: 30 ml/min

The operations are monitored by analytical HPLC (see Example 4.1). The group of fractions enriched in antibiotic A/16686 factor A2 aglycon are separated and combined.

Butanol is added to prevent foaming and the solvents are evaporated under vacuum. The residue (500 mg, 75% titre) is purified again by preparative HPLC with the same apparatus described above. Five portions of 100 mg are dissolved in 5 ml (each portion) of a mixture of water and acetonitrile 1:1 (v/v) and chromatographed eluting with a mixture of 0.05 M $HCOONH_4$:$CH_3CN$ 62:38 (v/v). The fractions containing the pure component are pooled; the solvents are evaporated under vacuum while repeatedly adding butanol to obtain a residual butanolic solution (100 ml). The solution is washed with a saturated water solution of NaCl (7×50 ml) until no residual $HCOONH_4$ is present. The organic phase is concentrated under vacuum to a volume of 20 ml and the precipitate is filtered off and washed with a little butanol. The filtrate and washing are evaporated to dryness. To the solid residue dissolved in 4 ml of water, 10% HCl is added to pH 3.5 and the precipitate formed is filtered off on a MILLIPORE® filter. The solution is lyophilized obtaining 120 mg of pure A/16686 factor A2 aglycon dihydrochloride.

Example 2

A/16686 factors A1, A2, A3 aglycons

A solution of 10 g of A/16686 complex (obtained according to U.S. Pat. No. 4,303,646) in a mixture of 180 ml of anhydrous dimethylformamide and 60 ml of butanol, containing 2.3% (w/v) of HCl is heated at 70°–75° C. (bath temperature) for 2 hours with stirring. After cooling at 0° C. the reaction mixture is brought to pH 4 with solid $NaHCO_3$, filtered and the butanol is evaporated under vacuum in a rotary apparatus. By adding ethyl ether a precipitate forms. After standing at −15° C. overnight the surnatant is discharged and the residual solvents are evaporated under vacuum. The oily residue (6 g) is dissolved with 100 ml of a mixture of water and acetonitrile 1:1 (v/v) and charged on a chromatographic column (600 mm×65 mm) containing 800 g of silanized SILICA GEL (70–230 mesh) (Merck) prepared by slurring with methanol, washing with 2 liters of water, conditioning with 2 liters of 2% aqueous $HCOONH_4$, and finally washing with water.

Water (1 liter) is passed through the column, followed by 1% (w/v) HCl (2 liters). Finally, the column is eluted successively with a mixture of 1% HCl:$CH_3CN$, 90:10 (2 liters); 1% HCl: $CH_3CN$, 85:15 (2 liters) and 1% HCl:$CH_3CN$, 75:25 (2 liters). Fractions of 30 ml each are collected and checked by analytical HPLC (see Example 4.1). The groups of fractions containing respectively the aglycons of A/16686 factors A1, A2 and A3 are pooled; butanol is added and the solvents are evaporated under vacuum to dryness.

The portion containing aglycon factor A2 is dissolved in a few milliliters of diluted HCl and lyophilized, obtaining 1.05 g of pure A/16686 factor A2 aglycon dihydrochloride.

The portion containing aglycon factor A1 (0.9 g) is dissolved in 30 ml of water: acetonitrile, 1:1, and the solution is charged on a chromatographic column containing 800 g of silanized SILICA GEL 60 (Merck) prepared as described above. The column is washed with 1 liter of water, then with 2 liters of 1% HCl and finally eluted with 1% HCl:$CH_3CN$ mixtures of the following proportions: 90:10 (2 liters); 85:15 (1 liter); 80:20 (1 liter); 75:25 (1 liter) .

Fractions of 30 ml are collected and checked by analytical HPLC (see Example 4.1). Fractions 250–280 containing aglycon factor A1 are pooled and evaporated to dryness after adding butanol. The solid residue (300 mg) is purified by semi-preparative HPLC using the following apparatus for each portion of 20 mg dissolved in 2 ml of a mixture of water and acetonitrile 1:1. Instrument: HEWLETT-PACKARD liquid chromatograph, Mod. 1080 equipped with a UV detector set at 254 nm, and a RHEODYNE injector with 200 microliters loop. Column: HIBAR LICHROSORB RP 8, 7 micron, 250 mm×10 mm (Merck)

Mobile phase: 0.05 M $HCOONH_4$:$CH_3CN$ (55:45), pH 4

Flow rate: 5.5 ml/min

Fractions containing pure aglycon factor A1 are collected, combined and, after addition of butanol, evaporated under vacuum to dryness. The residue is dissolved in a little water and lyophilized until $HCOONH_4$ is present. The residue is re-dissolved in a few milliliters of diluted HCl and lyophilized obtaining 140 mg of pure A/16686 factor A1 aglycon dihydrochloride.

The fractions containing aglycon A3 (0.08 g) is dissolved in 30 ml of water and the solution is charged on a chromatographic column containing 800 g of silanized SILICA GEL 60 (Merck) prepared as described above. The column is washed with 1 liter of water and eluted with a 1% HCl:$CH_3CN$, 75:25 mixture (10 liters).

Fractions of 30 ml are collected and checked by HPLC. Fractions 191–230 are combined and butanol is added thereto. The solvents are evaporated under vacuum and the residue is desalted, re-dissolved in diluted HCl and then lyophilized as described for factor A1, obtaining 300 mg of pure A/16686 factor A3 aglycon dihydrochloride.

Example 3

A/16686 tetrahydro factors A1, A2, A3 aglycons

A sample of 10 grams of mixture of A/16686 tetrahydrogenated factors A1, A2, A3, A'1, A'2 and A'3 obtained as in European Patent Appln. Ser. No. 88119001.1 (corresponding to U.S. patent application Ser. No 280035) is hydrolyzed for 3 hours under the conditions of Example 2. The reaction mixture is processed as in Example 2 and the tetrahydrogenated aglycons are recovered as dihydrochlorides.

Example 4

Analytical assays and physico-chemical characterization 4.1 - Analytical HPLC

Apparatus: HEWLETT-PACKARD liquid chromatograph, mod. 1084 B equipped with a UV detector set at 254 nm.

Column: ERBASIL C-18, 10 micron, 250 mm×4.6 mm (Carlo Erba).

Mobile phase:

A) 0.05 M $HCOONH_4$

B) $CH_3CN$

Flow rate: 1.5 ml/min

Gradient profile:

| min | 0 | 15 | 16 | 28 | 30 |
|---|---|---|---|---|---|
| % B | 38 | 38 | 55 | 55 | 38 |

Under these conditions the retention times ($t_R$) are as follows:

|  | $t_R$ (minutes) |
|---|---|
| Antibiotic A/16686 factor A1 aglycon | 14.40 (6.82) |
| Antibiotic A/16686 factor A2 aglycon | 19.33 (9.69) |
| Antibiotic A/16686 factor A3 aglycon | 20.96 (12.85) |

The values for the respective di-mannosylated compounds are reported in brackets.
Antibiotic A/16686 tetrahydro factor A1 aglycon 17.40 (8.97; 10.66)
Antibiotic A/16686 tetrahydro factor A2 aglycon 20.38 (12.24; 15.33)
Antibiotic A/16686 tetrahydro factor A3 aglycon 22.65 (19.03; 20.55)
The values for the respective di- and mono-mannosylated compounds are reported in brackets.

4.2 - Amino acid analysis and $^1$H NMR spectra

The acid hydrolysis is performed on the A/16686 aglycons with 6N HCl at 105° C. for 20 hours. The mixture of amino acids is separated by column chromatography on a strongly acidic sulfonic divinylbenzene resin (DOWEX 50 W) by eluting with aqueous HCl of increasing concentrations from 0.05N to 2N.

The amino acids are identified by comparison with authentic samples on the basis of $^1$H NMR and GC-MS. The amino acid ratio and their sequence in the intact molecules are determined by NMR experiments.

All compounds show the same amino acids compositions and sequence.

The following Table III shows the type and number of amino acid residues in each of the aglycons.

Two equivalents of ammonia per mole of each aglycon is titrated in the respective acid hydrolysis mixtures by means of an amino acid automatic analyzer providing evidence of two primary amide groups. Furthermore, the total number of nitrogen atoms (19) resulting from $^{15}$N NMR experiments exceeds by two the number of nitrogen atoms involved in the peptide bonds according to the number of aminoacids in the molecule (Table III) and titration of the aglycons does not show any presence of free carboxylic groups. These considerations support that the two primary amide groups are on the aspartic and threo-beta-hydroxyaspartic acid units, respectively.

The $^1$H NMR spectra are recorded on a BRUCKER AM 500 spectrometer equipped with an Aspect 3000 computer at 500 MHz. The following Table IV shows the chemical shifts (delta, ppm) of antibiotic A/16686 factor A2 aglycon in $D_2O$:DMSO, 4:1 at pH 4.6, temperature 40° C., internal standard TMS (delta=0.00 ppm).

Figure 1:
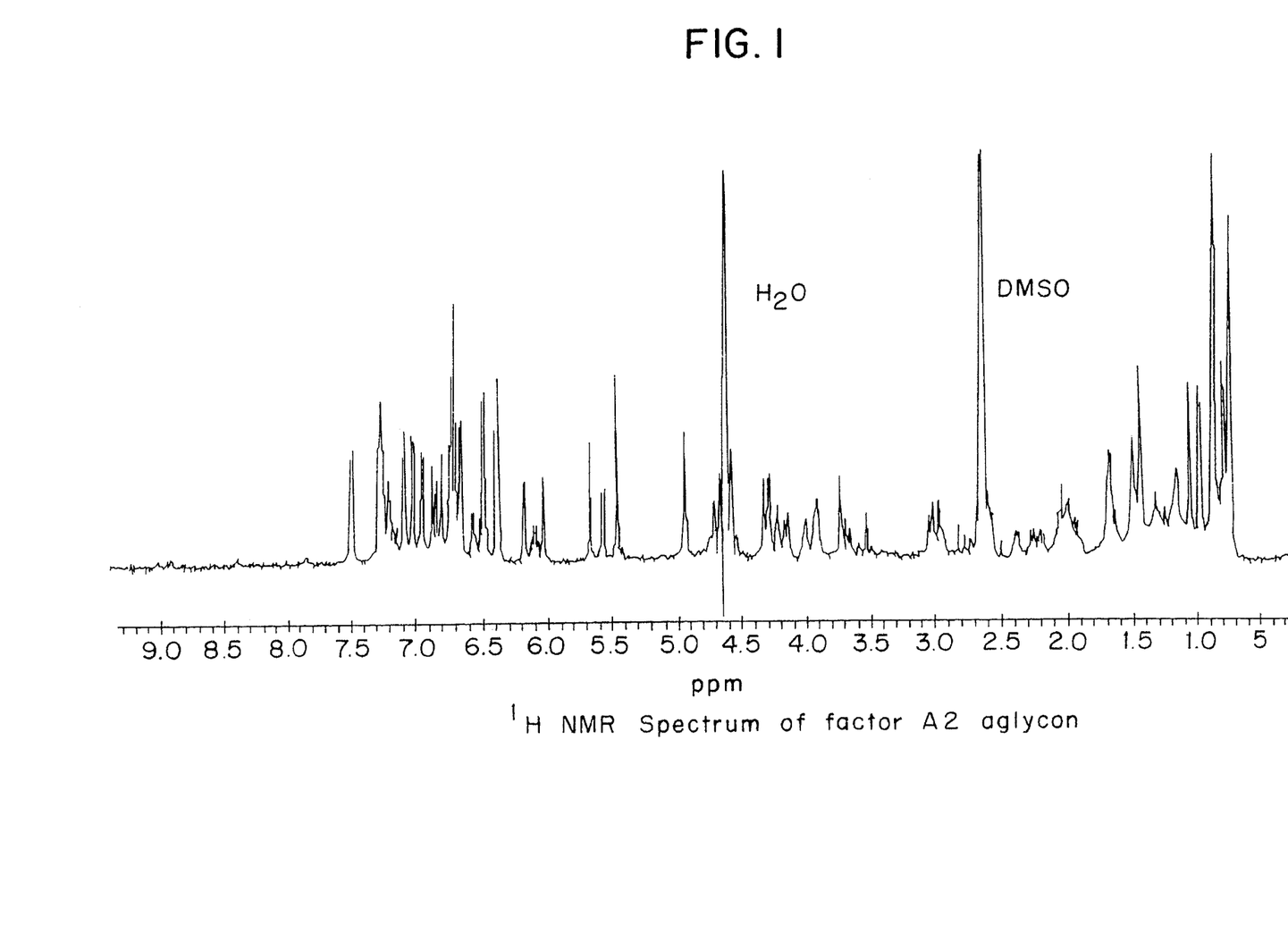
FIG. 1 depicts the $^1$H NMR Spectrum of factor A2 aglycon.

FIG. 1 reports the $^1$H NMR spectrum of factor A2 aglycon. The $^1$H NMR spectra of the other aglycons are substantially identical to the one of the aglycon of factor A2 apart from the signals attributed to the fatty acid chains attached to the asparagine moiety. In all spectra the signals corresponding to the sugar moieties are absent. The spectra of the tetrahydro aglycons do not show the resonance signals of the vinylic protons of the fatty acids side-chains.

TABLE IV

| Amino acid | $HC_{alpha}$ | $HC_{beta}$ | others |
|---|---|---|---|
| 1 Aspartic acid | 4.70 | 2.25, 2.05 | — |
| 2 Beta-hydroxyaspartic acid | 5.53 | 5.83 | — |
| 3 4-Hydroxyphenylglycine | 6.21 | — | Phenyl 7.44 (b, f), 6.98 (c, e) |
| 4 Ornithine | 4.22 | 1.97, 1.71 | — |
| 5 Threonine | 4.38 | 4.01 | $HC_{gamma}$ 1.05 |
| 6 4-Hydroxyphenylglycine | 6.78 | — | Phenyl 6.75 (b, f), 6.39 (c, e) |
| 7 4-Hydroxyphenylglycine | 5.48 | — | Phenyl 6.73 (b, f), 6.47 (c, e) |
| 8 Threonine | 3.74 | 3.92 | $HC_{gamma}$ 0.81 |
| 9 Phenylalanine | 4.93 | 1.97, 1.71 | Phenyl 7.23 (b, f), 6.94 (c, d, e) |
| 10 Ornithine | 4.18 | 2.25, 1.88 | $HC_{gamma}$ 1.67, $HC_{delta}$ 2.98 |
| 11 4-Hydroxyphenylglycine | 6.88 | — | Phenyl 7.26 (b, f), 6.64 (c, e) |
| 12 Threonine | 4.68 | 3.93 | $HC_{gamma}$ 0.94 |
| 13 4-Hydroxyphenylglycine | 6.07 | — | Phenyl 7.06 (b, f), 6.67 (c, e) |
| 14 Glycine | 3.79, 3.02 | — | — |
| 15 Leucine | 4.36 | 1.47 | $HC_{gamma}$ 1.47, $HC_{delta}$ 0.73 |
| 16 Alanine | 4.22 | 1.45 | — |
| 17 3-Chloro-4-hydroxyphenylglycine | 5.01 | — | Phenyl 6.82 (f), 6.53 (b), 6.33 (e) | fatty acid side chain: 5.58 ($HC_{alfa}$); 6.07 ($HC_{delta}$); 6.53 ($HC_{beta}$); 7.25 ($HC_{gamma}$); 1.98 ($CH_2$); 1.68 ($HC_{zeta}$); 0.85 ($2CH_3$)

TABLE III

| Amino acid | Number of units |
|---|---|
| Threo-beta-hydroxyaspartic acid | 1 |
| Aspartic acid | 1 |
| Allothreonine | 3 |
| Glycine | 1 |
| Alanine | 1 |
| 4-Hydroxyphenylglycine | 5 |
| Leucine | 1 |
| Phenylalanine | 1 |
| 3-Chloro-4-hydroxyphenylglycine | 1 |
| Ornithine | 2 |

4.3 - Lactone ring

The presence of a lactone ring is supported by the absorbance at 1760 cm$^{-1}$ in the IR spectrum (see under Example 4.4). The position of the lactone bond is established by a) identification of the amino acid contributing to the lactone bond with its carboxylic group b) identification of the hydroxy-amino acid contributing to the lactone bond with its hydroxyl group.

According to step a) factor A2 aglycon is reduced with $Ca(BH_4)_2$ and then hydrolyzed with concentrated HCl as described in the copending European Patent Application Ser. No. 88119001.1 (corresponding to U.S. patent application Ser. No. 280035). The presence of the 2-amino-2-(3-chloro- 4-hydroxyphenyl)ethanol in the hydrolyzate confirms the position of the carboxylic moiety forming the lactone bond in the aglycons structure formula I.

According to step b) factor A2 aglycon is reacted with phenylisocyanate and then hydrolyzed as described in European Patent Application Ser. No. 88119001.1 (corresponding to U.S. patent application Ser. No. 280035). The constant amount of hydroxyaspartic acid versus the decrease of the other hydroxylated aminoacids confirms the position of the hydroxy group involved in the lactone bond in the aglycons structure formula I.

4.4 - I.R. Spectra

Figure 2:
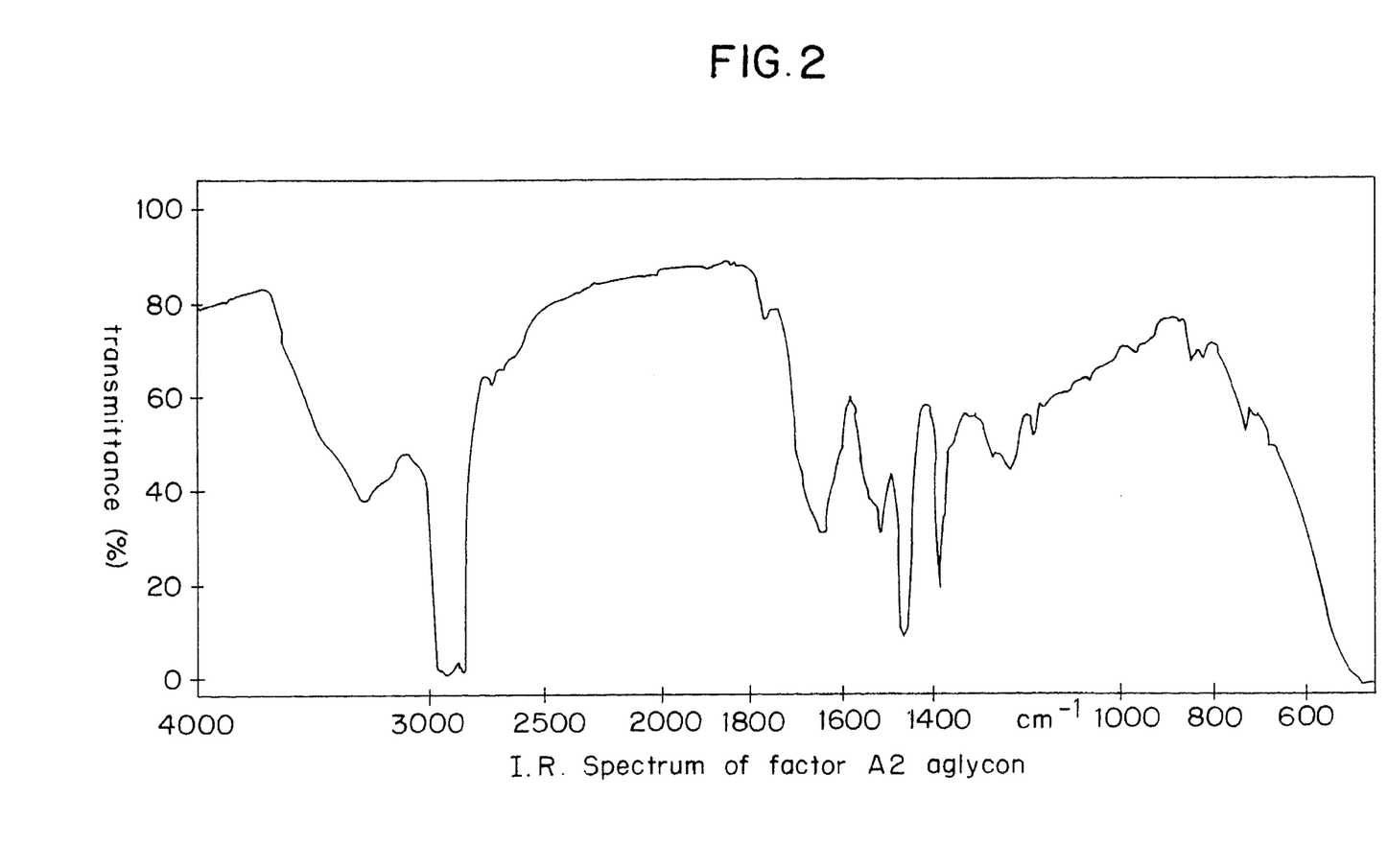
FIG. 2 depicts the I.R. spectrum of factor A2 aglycon.

The I.R. spectrum of factor A2 aglycon recorded as nujol mull with a PERKIN-ELMER (mod. 500) spectrophotometer is shown in FIG. 2 of the accompanying drawings. The following absorption maxima are observed: 3700–3100 (ny NH and ny OH), 3020–2800 (nujol), 1760 (ny C=O lactone), 1640 (ny C=O, amide I), 1510 (delta NH, amide II), 1460 and 1375 (nujol), 1230 (ny C-O, lactone), 840 and 815 $cm^{-1}$ (gamma CH aromatics).

The spectra of the other aglycons do not show substantial differences.

4.5 - U.V. Spectra

Figure 3:
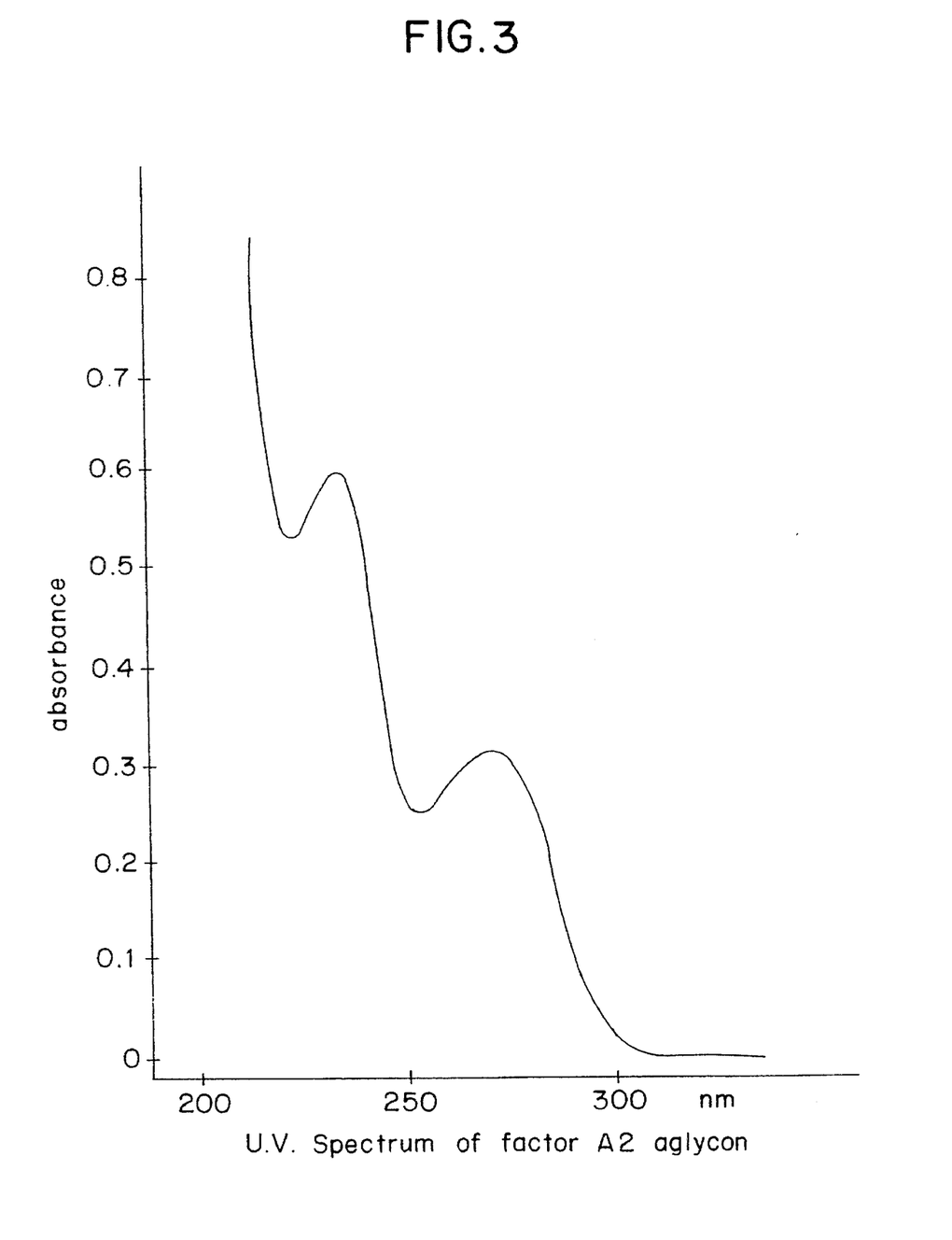
FIG. 3 depicts the μv spectrum of factor a2 aglycon.

The Ultraviolet Spectrum of factor A2 aglycon registered in 0.1N HCl with a PERKIN ELMER mod. 320) spectrophotometer is given in FIG. 3 of the accompanying drawings. The spectrum exhibits the following absorption maxima: 233 nm (E 1%, 1 cm 206.7) and 271 nm (E 1%, 1 cm 109.3).

The U.V. spectra of the other unsaturated aglycons do not show substantial differences. The tetrahydro aglycons exhibit absorption maxima at 232 and 275 nm.

4.6 - FAB-MS Spectra

The Fast Atom Bombardment Mass Spectra (FAB-MS) are recorded with a MS-50-TC instrument using glycerol as a matrix. Bombardment gas Xe; kinetic energy 6 keV; accelarating voltage 8 kV. The low mass isotope of the protonated molecular ions ($MH^+$) have molecular weights of 2214.9 (factor A1 aglycon), 2228.9 (factor A2 aglycon) and 2242.9 (factor A3 aglycon). The tetrahydro aglycons protonated molecular ions ($MH^+$) indicate molecular weights of 2218.9, 2232.9 and 2246.9, respectively.

These data are within 0.3 dalton of the theoretical ones and are in agreement with the structures assigned.

4.7 - Elemental analysis

The elemental analysis gives the following approximate percentage composition:

Example 5

Representative examples of lotions, solutions and gel 5.1 - Lotion

A 2 percent (w/w) hydroalcoholic lotion is formulated with the following ingredients (for 100 g of lotion)

| | |
|---|---|
| Factor A2 aglycon | 2.00 g |
| Lactic acid 90% (w/w) solution | 0.107 g |
| Sodium hydroxide 10% (w/w) solution to pH 4 | equal masses to 100 g |
| Ethanol 96% | |
| Purified water BP | |

5.2 - Solution

Vials containing freeze-dried powder for reconstitution in normal saline to give a solution for wound infections or in a hydroalcoholic vehicle to provide lotions for topical use are prepared by dissolving respectively 10 mg, 25 mg, 50 mg and 100 mg of active aglycon in 1–2 ml of purified water BP, filling the vials and freeze drying to a residual moisture content of about 2%.

5.3 - Gel

A gel topical form can be prepared with the following ingredients:

| | |
|---|---|
| Active aglycon | 2.00 g |
| Lactic acid 90% (w/w) solution | 0.55 g |
| Methocel | 3.00 g |
| Ethanol 96% | equal masses to 100 g |
| Purified water BP | |

The active aglycon is dissolved in purified water, filtered and then the solution and the lactic acid are added at 25° C. to a methocel dispersion in the remaining water. After addition of ethanol and mixing to complete the dispersion, the pH value is adjusted to 4.0 by addition of 10% sodium hydroxide.

We claim:

1. A compound of the formula:

| | factor A1 aglycon | factor A2 aglycon | factor A3 aglycon | tetrahydro factor A1 aglycon | tetrahydro factor A2 aglycon | tetrahydro factor A3 aglycon |
|---|---|---|---|---|---|---|
| *C% | 55.0 | 53.8 | 54.9 | 55.2 | 56.3 | 55.4 |
| *H% | 5.3 | 6.0 | 5.8 | 5.8 | 6.2 | 6.3 |
| *N% | 12.4 | 11.9 | 13.1 | 12.2 | 13.0 | 12.2 |
| Cl% | 4.7 | 5.1 | 4.8 | 4.8 | 4.6 | 4.6 |
| Ashes % | 0.5 | 0.3 | 0.7 | 0.5 | 0.2 | 0.2 |
| **Weight loss % | 8.4 | 11.2 | 7.9 | 7.3 | 6.8 | 6.5 |

*The sample has been previously dried at about 140° C. under inert atmosphere.
**Thermogravimetric analysis The values are in agreement with those calculated for the respective di-hydrochloride salts.

in which R is represented by a substituent selected from the group consisting of -CO-CH=CH-CH=CH-CH$_2$-CH$_2$-CH$_3$,
-CO-CH=CH-CH=CH-CH$_2$-CH(CH$_3$)$_2$,
-CO-CH=CH-CH=CH-CH-CH$_2$-CH$_2$-CH(CH$_3$)$_2$,
-CO(CH$_2$)$_6$-CH$_3$,-CO(CH$_2$)$_5$CH(CH$_3$)$_2$ and
-CO(CH$_2$)$_6$CH(CH$_3$)$_2$, a pharmaceutically acceptable acid addition salt thereof, or a mixture of said compounds present in any proportion.

2. A compound of claim 1 wherein

R is represented by:

-CO-CH=CH-CH=CH-CH$_2$-CH$_2$-CH$_3$,
-CO-CH=CH-CH=CH-CH$_2$-CH(CH$_3$)$_2$ or
-CO-CH=CH-CH=CH-CH$_2$-CH$_2$-CH(CH$_3$)$_2$ or a pharmaceutically acceptable acid addition salt thereof.

3. A compound of claim 1 wherein R is represented by:

-CO(CH$_2$)$_6$-CH$_3$,-CO(CH$_2$)$_5$CH(CH$_3$)$_2$ or

-CO(CH$_2$)$_6$CH(CH$_3$)$_2$ or a pharmaceutically acceptable acid addition salt thereof.

4. A topical pharmaceutical formulation for the treatment of wound infection or acne comprising an antibacterially effective amount of a compound of claim 1 in admixture with a pharmaceutically acceptable carrier.

5. A method for combatting infectious diseases in mammals comprising administering an antibacterially effective amount of a compound of claim 1 to a mammal in need thereof.

6. A method of claim 5 wherein the infectious disease is a wound infection or acne and the compound is topically administered.

* * * * *